US00PP10402P

United States Patent [19]

Hureau

[11] Patent Number: Plant 10,402

[45] Date of Patent: May 19, 1998

[54] STRAWBERRY PLANT VARIETY NAMED DARSELECT

[75] Inventor: Robert Hureau, Noisy-sur-Ecole, France

[73] Assignee: Societe Civile Darbonne, Milly-La-Foret, France

[21] Appl. No.: 704,273

[22] Filed: Aug. 28, 1996

[51] Int. Cl.[6] ..... A01H 5/00

[52] U.S. Cl. ..... Plt./48

[58] Field of Search ..... Plt./48

[56] References Cited

U.S. PATENT DOCUMENTS

P.P. 2,884 5/1969 Hagerstrom ..... Plt./48

P.P. 5,071 7/1983 Johnson ..... Plt./48

P.P. 5,300 10/1984 Johnson ..... Plt./48

P.P. 6,578 1/1989 Voth et al. ..... Plt./48

OTHER PUBLICATIONS

GTITM UPOVROM listing FRPBR101017 for 'DARSELECT' Oct. 10, 1996.

*Primary Examiner*—James R. Feyrer

*Attorney, Agent, or Firm*—Christie, Parker & Hale, LLP

[57] ABSTRACT

A strawberry plant producing large conical fruit on a vigorous plant having good rooting capacity.

2 Drawing Sheets

BACKGROUND OF THE INVENTION

This disclosure involves a newly developed strawberry, *Fragaria Xannanassa* Duch. plant, which has been denominated 'Darselct' for purposes of international recognition. The new variety of strawberry was created by my crossing as female parent the variety known as 'Elsanta' and as male parent the variety known as 'Parker'.

The new variety was grown and asexually reproduced by runners and micropropagation. The plant of this invention is the resulting selection, from the stated cross, which was based on a novel and superior combination of characteristics which will be disclosed infra, as well as depicted in the drawing. The combination of characteristics reflects the novelty of this plant and of its potentially advantageous use in the production of commercial strawberry fruit as well as in planned breeding programs for the development of further superior varieties. Asexual propagation and testing in Milly La Foret, France, has demonstrated that the combination of traits disclosed herein which characterize the new variety are fixed and retained true-to-type through successive generations of asexual reproduction.

SUMMARY OF THE INVENTION

The present invention relates to a new and distinct strawberry variety. The varietal denomination of the new variety is 'Darselect'. Among the characteristics which distinguish the new variety from other varieties of which I am aware are a combination of traits which include vigorous growth habit, good rooting capacity, large conical fruit with firm skin, early ripening and long harvest time. The new variety is not ever bearing. The new strawberry plant 'Darselect' is a short day responsive plant.

Comparison to Closest Variety

The new variety is closest to the variety 'Elsanta', but is distinguished therefrom by producing a more erect plant, longer petioles, larger fruit and more homogenous skin color than 'Elsanta'.

BRIEF DESCRIPTION OF ILLUSTRATION

The accompanying photographs show typical specimens of the new variety, including fruit, foliage and flower, in color as nearly true as it is reasonably possible to make in color illustrations of this character.

DESCRIPTION OF THE NEW VARIETY

Figure 1:
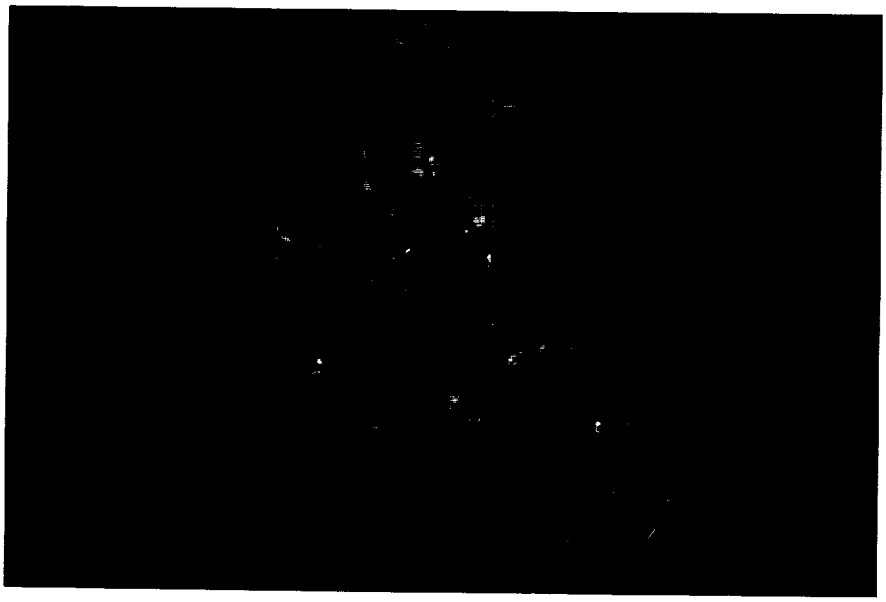
FIGS. 1 and 2 show typical fruit and fruit in cross section, and illustrate the flesh, flesh coloration, and conical shape.
Figure 2:
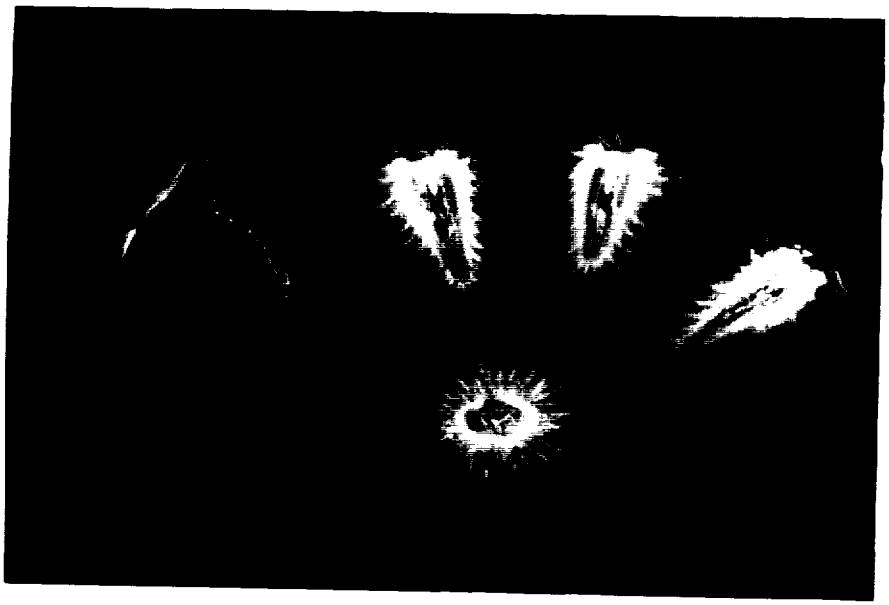
Figure 3:
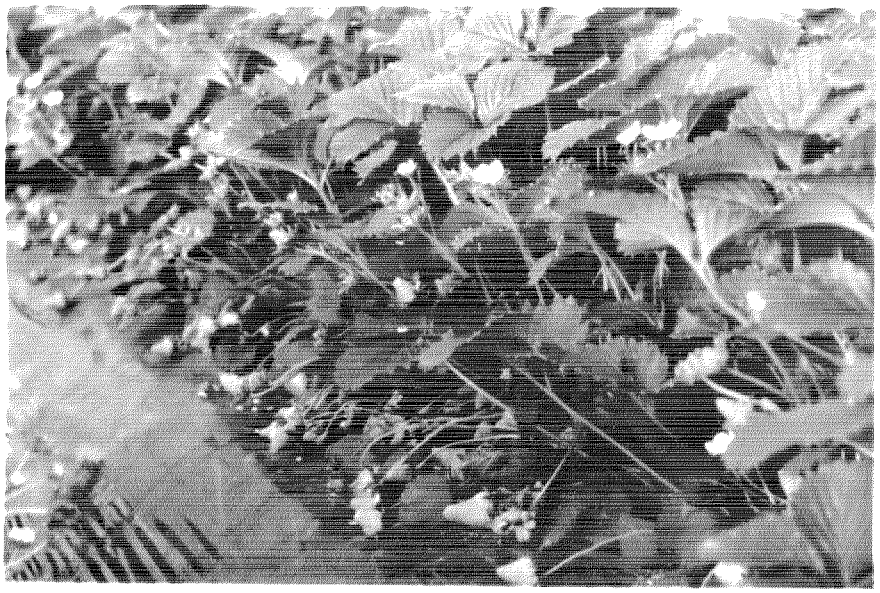
FIGS. 3 and 4 show plants of the new variety, plants with fruit, and foliage.
Figure 4:
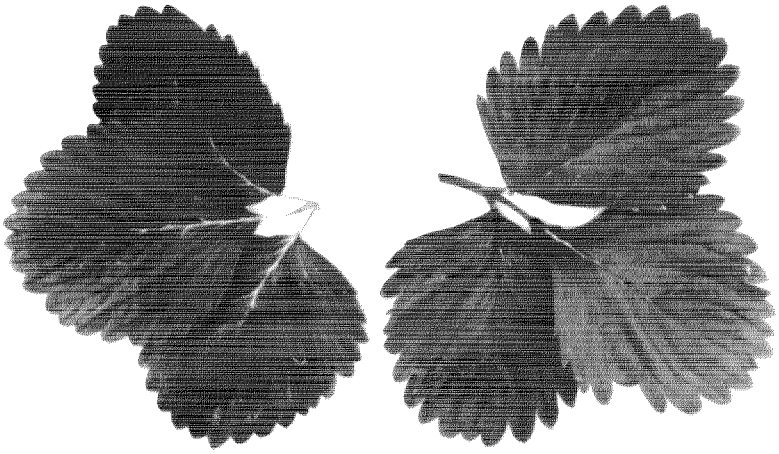

The following detailed description of the new variety is based upon observations taken of plants and fruit grown outdoors in Milly La Foret, France, in June.

Description of the New Variety and Comparison with 'Elsanta'

| | DARSELECT | ELSANTA |
|---|---|---|
| PLANT: | | |
| Habit: | Globose | Globose, flattened |
| Density: | Medium | Medium to strong |
| Vigor: | Very vigorous | Medium vigorous |
| Size: | High | Medium to high |
| Crowns, Branches: | Usually about 3 crowns for one plant; usually about 4 branches for one crown; usually about 12 branches for one plant | |
| Size of Crown: | 80% between 9 to 15 mm | |
| Yield: | About 800 g to 900 gr for one plant | |
| Chilling requirement: | About 900 hours = summ temperatures below or equal to +7° C. | About 1200 hours |
| Preferred planting time: | Early July | |
| Peak production: | June | |

US00PP10403P

United States Patent [19]

Jessel, Jr.

[11] Patent Number: Plant 10,403

[45] Date of Patent: May 19, 1998

[54] CARNATION PLANT NAMED 'CFPC DELICADO'

[75] Inventor: Walter H. Jessel, Jr., Gonzales, Calif.

[73] Assignee: California Florida Plant Co., L.P., Salinas, Calif.

[21] Appl. No.: 711,032

[22] Filed: Sep. 10, 1996

[51] Int. Cl.[6] ..... A01H 5/00

[52] U.S. Cl. ..... Plt./70.2

[58] Field of Search ..... Plt./70.2

*Primary Examiner*—Howard J. Locker
*Attorney, Agent, or Firm*—Christie, Parker & Hale, LLP

[57] ABSTRACT

A new variety of carnation plant producing light orange flowers.

1 Drawing Sheet

SUMMARY OF THE INVENTION

The present invention relates to a new and distinct variety of carnation plant which was originated by crossing as female parent the variety known as 'CFPC Sunset' (U.S. Plant Pat. No. 7,855) and as male parent an undistributed, unpatented seedling identified as 920205. The varietal denomination of this new carnation is 'CFPC Delicado'.

Among the novel combination of characteristics possessed by the new variety which distinguishes it are very good Fusarium sp. tolerance and medium, sprays of light orange flowers with red markings.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypic expression may vary depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: 'CFPC Delicado'.

Classification:

*Botanical.*—*Dianthus caryophyllus.*

*Commercial.*—Carnation, spray-type.

Parentage:

*Female parent.*—'CFPC Sunset'.

*Male parent.*—920205.

1. Plant:

*Height.*—About 39 inches (first flowering).

*Growing habit.*—Herbaceous, semi-upright.

*Blooming habit.*—As a spray.

*Blooming season.*—Year round.

*Rooting time.*—About 18–20 days.

*Mutation prone.*—No.

*Disease resistance.*—Very good.

*Temperature tolerance.*—Wide range.

*Breaking action.*—Very good, about 8 to 9 lateral shoots per plant.

2. Foliage:

*Color.*—Upper side: Near 137B. Lower side: Near 137A.

*Size.*—About 5¾ inches long, about ⅛ inches wide.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Near 137A.

3. Bud:

*Shape.*—Ovoid.

*Color.*—Near 138A.

*Length.*—About 1⅛ inches.

*Diameter.*—About ½ inch.

4. Calyx:

*Number of sepals.*—About 6.

*Length.*—About ⅞ inch.

*Width.*—About ¼ inch.

*Color.*—Outside— Near 144A. Inside— Near 145A.

5. Bloom:

*Shape.*—Round.

*Size.*—Diameter average: About 2½ inches. Depth average: About ¾ inches.

*Borne.*—Terminal as a spray, approximately 10 open flowers and buds per spray, stem length approximately 39 inches.

*Color.*—General tonality: Light orange, very slight picotee red. Upper side: Near 27A, lightens to near 27B toward extremities and in the petals at center; picotee edge is near 44B on the tops. Lower side: Near 27B, picotee edge near 44C (on reverse). Center: Near 27B. Outer petals: Near 27B with near 44B.

*Keeping quality.*—Good, petals dry up after about 2 to 3 weeks and remain attached.

*Fragrance.*—Very slight.

6. Petals:

*Number.*—About 32.

*Outer petals.*—Length: About 1 ¾ inches. Width: About 1 inch.